(12) United States Patent
Walther et al.

(10) Patent No.: US 10,751,522 B2
(45) Date of Patent: Aug. 25, 2020

(54) BI-DIRECTIONAL CANNULA

(71) Applicant: Edwards Lifesciences Corporation, Irvine, CA (US)

(72) Inventors: Thomas Walther, Irvine, CA (US); Mark M. Dehdashtian, Irvine, CA (US); Teodoro S. Jimenez, Irvine, CA (US); Norma A. Garcia, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 263 days.

(21) Appl. No.: 15/991,979

(22) Filed: May 29, 2018

(65) Prior Publication Data
US 2018/0272116 A1    Sep. 27, 2018

Related U.S. Application Data (62) Division of application No. 14/926,699, filed on Oct. 29, 2015, now Pat. No. 9,981,119.

(Continued)

(51) Int. Cl.
*A61M 39/22* (2006.01)
*A61M 25/00* (2006.01)
(Continued)

(52) U.S. Cl.
CPC .......... *A61M 39/22* (2013.01); *A61M 1/3659* (2014.02); *A61M 25/007* (2013.01);
(Continued)

(58) Field of Classification Search
CPC .......... A61M 25/0029; A61M 25/0041; A61M 2025/0034; A61M 25/0076; A61M 25/0681
See application file for complete search history.

(56) References Cited

U.S. PATENT DOCUMENTS

| 5,312,344 A | 5/1994 | Grinfeld et al. |
| 6,099,506 A | 8/2000 | Macoviak et al. |

(Continued)

FOREIGN PATENT DOCUMENTS

| EP | 0619745 A1 | 10/1994 |
| WO | 9964099 A1 | 12/1999 |
| WO | 2006093273 A1 | 9/2006 |

OTHER PUBLICATIONS

Int'l. Search Report for PCT/US2015/044003, dated Nov. 11, 2015.
Int'l. Search Report for PCT/US2015/036005, dated Sep. 21, 2015.

*Primary Examiner* — Nathan R Price
*Assistant Examiner* — Dung T Ulsh
(74) *Attorney, Agent, or Firm* — Richard B. Cates (57) ABSTRACT

A bi-directional cannula for perfusing blood in two directions. The cannula has a distal opening in fluid communication with a cannula first lumen. The cannula has a secondary opening proximal of the distal opening, and may include a movable tubular extension selectively extendable from the cannula via the secondary opening. The tubular extension may be in fluid connection with the cannula first lumen and/or a cannula second lumen. The tubular extension may have distal and/or side openings, with the openings providing antegrade fluid perfusion. The cannula second lumen may be separate from the first lumen, so that perfusion can be selectively provided to just the cannula distal opening, just the secondary opening/tubular extension, or simultaneously to both the distal opening and secondary opening/tubular extension.

20 Claims, 7 Drawing Sheets

Related U.S. Application Data (60) Provisional application No. 62/072,257, filed on Oct. 29, 2014.

(51) Int. Cl.
*A61M 1/36* (2006.01)
*A61M 25/06* (2006.01)

(52) U.S. Cl.
CPC .... *A61M 25/0029* (2013.01); *A61M 25/0041* (2013.01); *A61M 25/0043* (2013.01); *A61M 2025/0034* (2013.01); *A61M 2025/0039* (2013.01); *A61M 2025/0076* (2013.01); *A61M 2025/0681* (2013.01); *A61M 2210/08* (2013.01)

(56) References Cited

U.S. PATENT DOCUMENTS

| | | | |
|---|---|---|---|
| 6,197,014 B1 | 3/2001 | Samson et al. | |
| 6,533,770 B1 | 3/2003 | Lepulu et al. | |
| 6,626,872 B1 | 9/2003 | Navia et al. | |
| 6,669,674 B1 | 12/2003 | Macoviak et al. | |
| 8,343,091 B2 * | 1/2013 | Schweikert | A61M 25/003 604/28 |
| 8,795,227 B2 * | 8/2014 | Condado | A61M 25/0075 604/101.03 |
| 2003/0004452 A1 | 1/2003 | Lenker | |
| 2003/0149395 A1 * | 8/2003 | Zawacki | A61M 1/3653 604/40 |
| 2003/0176830 A1 | 9/2003 | Scheule | |
| 2005/0222532 A1 | 10/2005 | Bertolero et al. | |
| 2006/0253088 A1 * | 11/2006 | Chow | A61M 25/003 604/284 |
| 2008/0009804 A1 * | 1/2008 | Rosetti | A61M 25/0029 604/173 |
| 2008/0183128 A1 * | 7/2008 | Morriss | A61M 3/0283 604/35 |
| 2009/0234291 A1 | 9/2009 | Saunders et al. | |
| 2010/0241068 A1 | 9/2010 | Chen | |
| 2011/0152741 A1 | 6/2011 | Banchieri et al. | |
| 2012/0016408 A1 | 1/2012 | Barbut et al. | |
| 2012/0259273 A1 | 10/2012 | Moshinsky et al. | |
| 2012/0302953 A1 | 11/2012 | Don Michael | |
| 2014/0135786 A1 * | 5/2014 | Sadanandan | A61M 25/0041 606/108 |
| 2015/0202406 A1 * | 7/2015 | Lim | A61M 25/007 604/528 |
| 2016/0096000 A1 * | 4/2016 | Mustapha | A61M 25/007 604/164.13 |

* cited by examiner

BI-DIRECTIONAL CANNULA

CROSS-REFERENCE TO RELATED APPLICATIONS

This application is a divisional of U.S. patent application Ser. No. 14/926,699, filed Oct. 29, 2015, now U.S. Pat. No. 9,981,119, which claims the benefit of U.S. Patent Application No. 62/072,257, filed Oct. 29, 2014, the entire disclosures of which are incorporated by reference in their entireties.

FIELD OF THE INVENTION

The present invention relates to the field of intraluminal devices, and more particularly to perfusion catheters for delivery of fluid to a patient's vascular system.

BACKGROUND OF THE INVENTION

Peripheral arterial cannulation is used during many cardiac surgeries, and is often performed via the femoral artery. Such cannulation is very effective in circulatory support scenarios for cardiorespiratory support, e.g., pulmonary bypass, for patients undergoing various surgical procedures. The cannulation supports a retrograde flow from the femoral artery into the heart, but regular (antegrade) flow is often compromised. The lack of regular antegrade flow results in compromised blood flow to the lower limb (e.g., the leg below the site at which the cannula is inserted into the artery). Such compromised blood flow to the lower limb is often acceptable for the relatively short times involved in many procedures, but in some circumstances it is desirable to provide some blood flow to the lower extremity during the procedure.

To provide increased blood flow to the lower extremity, the cannula may be provided with bi-directional fluid flow capability. Various bi-directional perfusion cannulas have been proposed. One approach has been to use a perfusion cannula with a diameter significantly smaller than the blood vessel lumen diameter in order to permit some blood to flow back over the perfusion cannula, but such systems must be carefully designed and positioned in order to assure appropriate blood flow in the retrograde and antegrade direction. Another approach has been to include an additional perfusion cannula, positioned away from the primary perfusion cannula, to provide antegrade blood flow to the lower extremity. This approach requires the extra cannula as well as an extra perfusion line, as well as associated extra hardware and monitoring. Additional surgeon time is required, as well as an additional puncture in the blood vessel and possible additional incisions in the patient.

Some have included a perfusion port at an antegrade side of the cannula through which blood may flow to the lower extremity. Examples include US Patent Publication 2012/0259273 to Moshinsky et al.; European Patent Application EP 0619745 to Fonger DLP; and U.S. Pat. No. 6,626,872 to Navia. However, such ports must be carefully positioned and constructed to provide proper perfusion flow and to permit easy retraction of the cannula from the artery after the procedure is completed. Sometimes the arterial wall can collapse or constrict against the perfusion port, or a perfusion port extension may interfere with deployment and/or withdrawal of the cannula from the patient.

What has been needed is a perfusion cannula that can selectively provide bi-directional perfusion flow without obstruction of the perfusion ports while also providing for easy deployment and withdrawal of the cannula. The present invention meets these needs.

BRIEF SUMMARY OF THE INVENTION

The present invention provides a system, device, and method for providing selective bi-directional perfusion to a blood vessel.

For purposes of this application, the term "antegrade" refers to the natural direction of blood flow within the patient's blood vessels, i.e., the direction of blood flow without introduction of any flow-diverting devices. "Retrograde" refers to the direction which is opposite to the natural direction of blood flow.

An embodiment of the invention is a perfusion cannula comprising a substantially tubular member for insertion into a patient's body lumen, the substantially tubular member comprising a proximal end, a distal end, a tubular member inner lumen extending from the proximal end to the distal end, a first opening at the distal end, the first opening configured to provide fluid flow from the tubular member inner lumen to the body lumen in a first flow direction, an elbow (which may be pre-formed or selectively formed by a user via controls or simple mechanical bending) positioned along the substantially tubular member proximal of the distal end, a second opening formed at the elbow, and a substantially tubular extension having a deployed configuration and a stowed configuration. In the deployed configuration the substantially tubular extension extends at least partially out of the second opening, and in the stowed configuration the substantially tubular extension does not extend out of the second opening. The substantially tubular extension comprises a tubular extension inner lumen, a tubular extension distal opening, and a tubular extension proximal opening, wherein in the deployed configuration the tubular extension inner lumen provides a fluid flow path from the tubular member inner lumen to the body lumen in a second flow direction, wherein the second flow direction is opposite to the first flow direction.

The second opening may comprise a valve which has an open and a closed configuration, wherein in the open configuration fluid may flow from the inner lumen to the body lumen via the second opening, and in the closed configuration fluid is prevented from flowing from the inner lumen to the body lumen via the second opening. The valve may be biased toward the closed configuration. The tubular extension when extended out of the second opening may hold the valve in the open configuration. The elbow, which may be pre-formed or manually formed by a user (e.g., using controls or application of direct bending moment), may be positioned on the cannula between 1 cm and 8 cm proximal of the cannula distal end. The second opening may be positioned adjacent the elbow, and may be positioned on the cannula between 1 cm and 8 cm proximal of the distal end.

The construction and dimensions of the substantially tubular extension should be selected to fit the particular application. For example, a tubular extension for femoral artery perfusion may be tapered for ease of insertion out of the main cannula and into the femoral artery. Such a tubular extension may have an inner lumen diameter of between 1 mm and 4 mm, an overall length of between 0.5 cm to 5 cm (or 1 mm to 10 cm), and/or in the deployed configuration may extend out of the secondary opening a distance of between 0.5 cm to 3 cm (or 0.5 mm to 10 cm). The substantially tubular extension may have a distal opening, a proximal opening, and/or one or more side openings through which perfusion fluid may easily flow.

Deployment and/or retraction of the tubular extension may be performed via a control such as a line secured to the substantially tubular member and passing along the cannula to the proximal end thereof, wherein movement of the line effectuates movement of the substantially tubular member from the stowed configuration to the deployed configuration. The substantially tubular member is biased to the stowed configuration.

The cannula may have a dedicated secondary lumen in fluid communication with the tubular extension. The dedicated secondary lumen may provide fluid from a dedicated secondary fluid source.

A system according to the invention may include the device discussed above, and also have a primary perfusion fluid source in controlled fluid communication with the primary lumen of the cannula. Where the cannula has a dedicated secondary lumen, a dedicated secondary perfusion fluid source may provide perfusion fluid to the secondary lumen. The dedicated secondary perfusion fluid source may provide perfusion fluid which is different from the perfusion fluid provided by the primary perfusion fluid source.

Methods according to the invention may include providing perfusion to a limb of a patient during peripheral artery cannulization, which may include: forming an incision in the patient from the patient's skin and into a selected blood vessel; advancing a perfusion catheter into the selected blood vessel via the incision, the perfusion catheter comprising a proximal end, a distal end, an inner lumen extending from the proximal end to the distal end. a first opening at the distal end, the first opening configured to provide fluid flow from the inner lumen to the body lumen in a first direction, an elbow positioned along the substantially tubular member proximal of the distal end, a second opening formed at the elbow and configured for providing fluid flow form the inner lumen to the body lumen in a second direction, wherein the second direction is opposite to the first direction, and a substantially tubular extension having a deployed configuration and a stowed configuration, wherein in the deployed configuration the substantially tubular extension extends at least partially out of the second opening, and in the stowed configuration the substantially tubular extension does not extend out of the second opening. The methods may further include positioning the perfusion catheter with the distal end and elbow within the blood vessel; providing blood flow to the inner lumen and out of the first opening; selectively providing blood flow to the inner lumen and out of the second opening by selectively advancing the tubular extension out of the second opening. The method may also include, prior to selectively advancing the tubular extension out of the second opening, monitoring the time of the bypass procedure and/or patient parameters such as oxygenation, blood pressure, pulse, etc.

Other objects and further features of the present invention will become apparent from the following description when read in conjunction with the attached drawings.

DESCRIPTION OF PREFERRED EMBODIMENTS

Disclosed herein are descriptions of various illustrated embodiments of the invention. The descriptions are not to be taken in a limiting sense, but are made merely for the purpose of illustrating the general principles of the invention. The section titles and overall organization of the present description are for the purpose of convenience only and are not intended to limit the present invention.

The devices, systems, and methods of the present invention are generally applicable to medical procedures. The device and method disclosed herein are of particular value during cardiac procedures where bi-directional perfusion is desired. The device has particular relevance to circulatory support scenarios for cardiorespiratory support, e.g., pulmonary bypass, for patients undergoing various surgical procedures. Those skilled in the art will appreciate, however, that the device and method are relevant to a variety of procedures.

Figure 1:
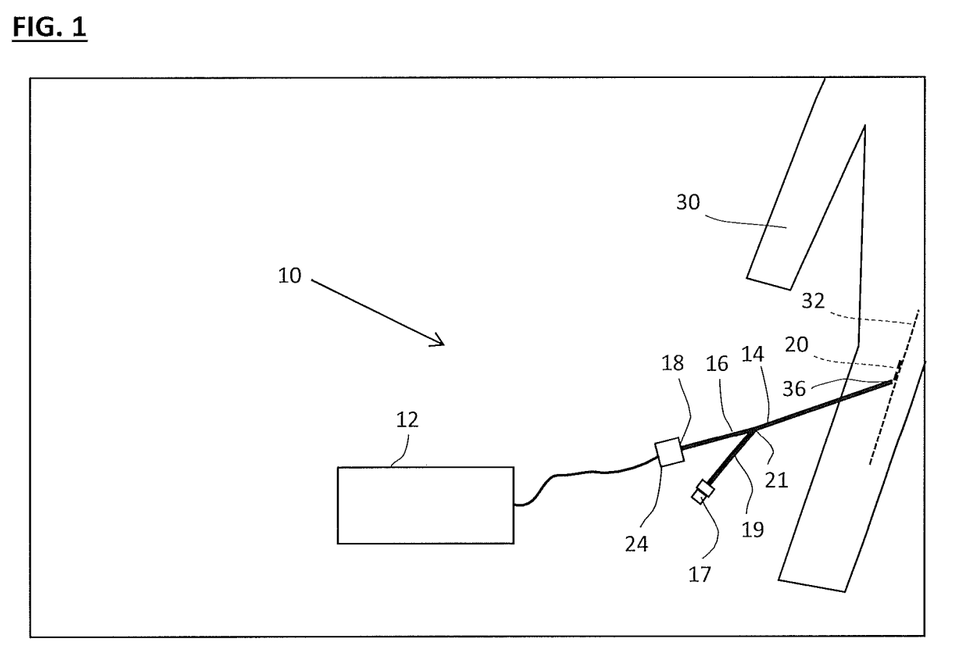
FIG. 1 depicts a front view of a system providing perfusion to a patient according to an embodiment of the invention.
Figure 2:
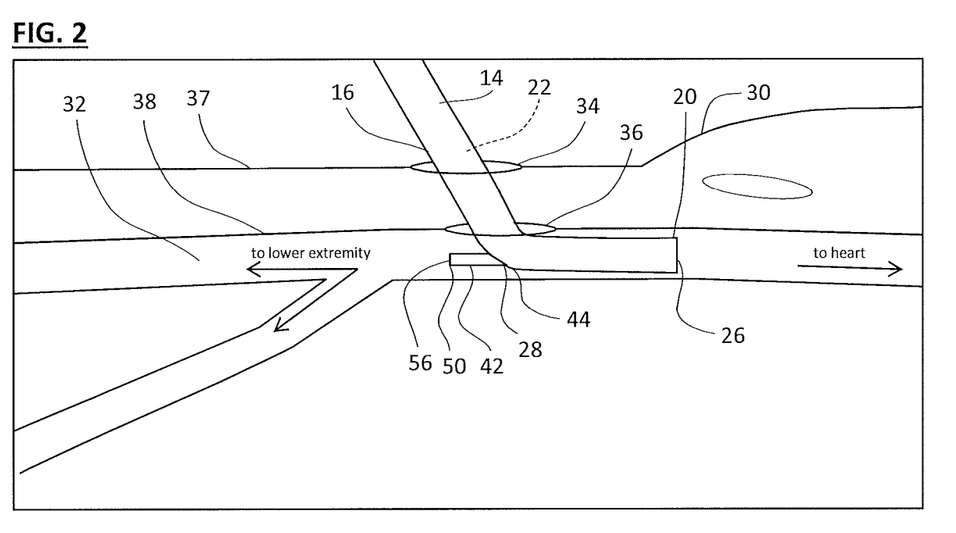
FIG. 2 depicts a side (close-up) view of the system of FIG. 1 providing perfusion to a patient according to an embodiment of the invention.

Referring to FIGS. 1 and 2 of the drawings, a system 10 comprises a perfusion fluid source 12 providing perfusion fluid to a perfusion cannula 14. The perfusion cannula 14 comprises an elongated body 16 having a proximal end 18 and a distal end 20.

A primary perfusion fluid lumen 22 extends through the elongated body 16 from the proximal fluid opening 24 (e.g., proximal access port) to a distal opening 26. The proximal fluid opening 24 may include a connector (not shown), such as screw-type connector, for securing the proximal opening 24 to the perfusion fluid source 12. The distal opening 26 may be positioned at the distal end 20 of the elongated body 16. A secondary opening 28 is positioned on the cannula elongated body 16 just proximal of the distal opening 26, and adjacent and/or just proximal to a bend 44, which may be between 10 to 60 degrees, in the cannula body just proximal of the distal end 20.

The cannula 14 may include a second proximal access port 17 leading to a second branch lumen 19 which connects to the elongated body 16 via a Y-connection 21 or similar connection. The second proximal access port 17 and second branch lumen 19 may be used for providing access to the patient's vasculature for various applications, such as for advancing a catheter (such as a treatment catheter) into the vasculature of the patient, e.g., advanced into second proximal access port 17 and second branch lumen 19 and into the femoral artery and then into the aorta and into the heart for treatment therein. The second proximal access port 17 and second branch lumen 19 may also, or alternatively, be used to provide perfusion fluid to the secondary opening 28. Note that additional proximal ports/openings and branch lumens may also be present, depending on the particular application, and used for fluid and/or instrument advancement into the patient.

FIG. 2 depicts a close-up view of the cannula distal end 20 positioned within the patient 30, and more specifically (in the particular embodiment depicted) positioned within the femoral artery 32, having been advanced into the femoral artery 32 via incisions 34, 36 in the patient's skin 37 and femoral wall 38, respectively. The cannula 14 may include a substantially tubular extension 42 having a distal end 50 with a tubular extension distal opening 56. The tubular extension distal end 50 is sized and positioned to be selectively advanced out of and back into the cannula body 16 via the secondary opening 28. Note that the distal opening 26, tubular extension 42 (and tubular extension distal opening 56), bend 44, and secondary opening 28 are all positioned within the femoral artery 32. In the embodiment depicted, fluid flowing from the distal opening 26 will travel in a retrograde manner toward the patient's heart, while fluid flowing through the secondary opening 28 via the substantially tubular extension 42 will travel in an antegrade manner toward the patient's lower extremity.

Figure 3A:
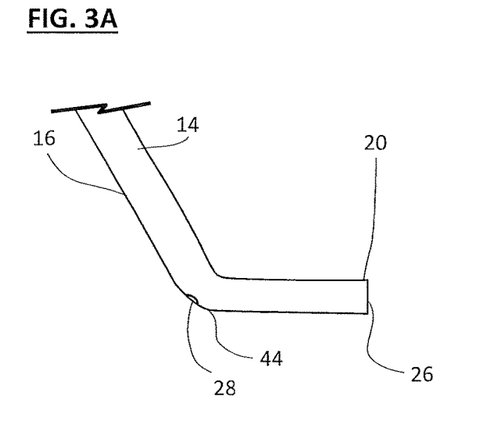
FIGS. 3A-3E depict side, side (cross-sectional), bottom, front, and back views of a distal portion of a device with a tubular extension stowed according to an embodiment of the invention.
Figure 3B:
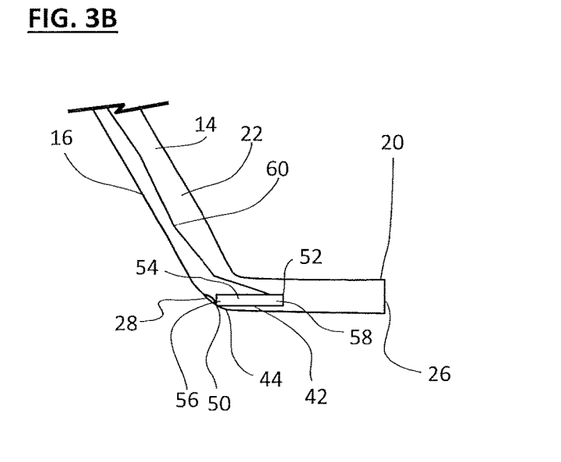
Figure 3C:
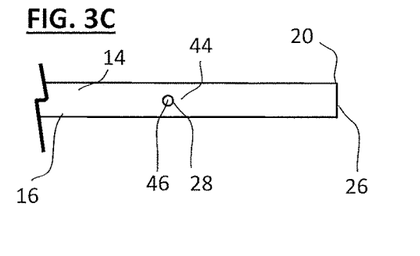
Figure 3D:
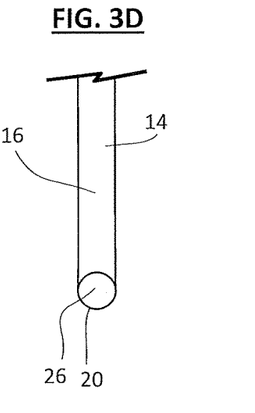
Figure 3E:
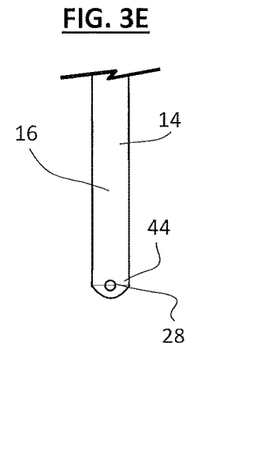
Figure 4A:
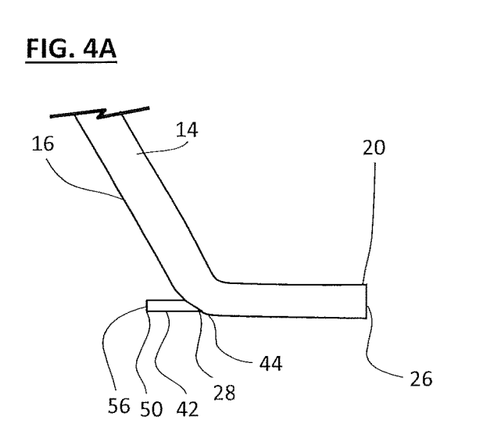
FIGS. 4A-4E depict side, side (cross-sectional), bottom, front, and back views of a distal portion of a device with a tubular extension deployed according to an embodiment of the invention.
Figure 4B:
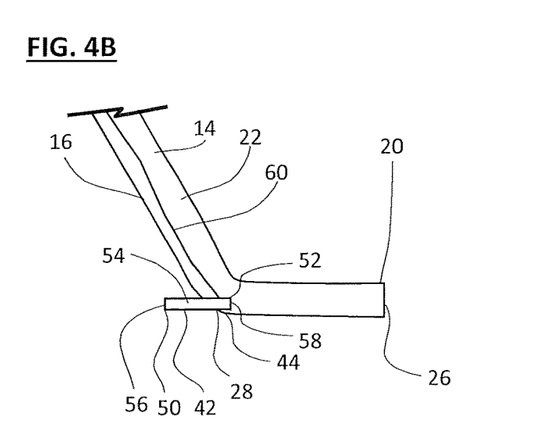
Figure 4C:
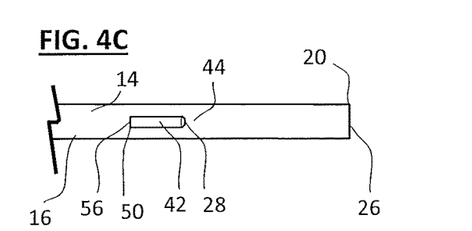
Figure 4D:
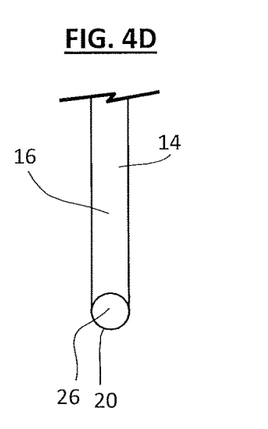
Figure 4E:
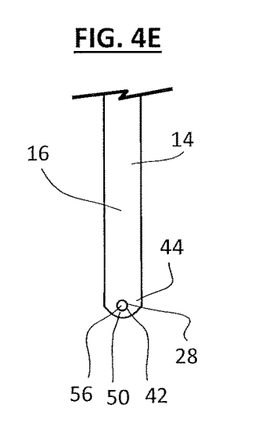

Controls may be positioned at the proximal end 18 of the device 12. The controls may be configured to control fluid flow through distal opening 26 and/or the secondary opening 28/tubular extension 42, and may control the movement of cannula components such as the substantially tubular extension 42 (e.g., via a control line 60 such as that depicted in FIG. 3B). The cannula overall dimensions can vary according to a particular application. For example, in various embodiments of the invention the cannula overall length may be between 20 and 40 cm, or about 30 cm. In various embodiments of the invention the distance from the Y-connector split to the distal end of the cannula may be between 15 cm and 20 cm, or about 17 cm. In various embodiments of the invention the working length of the cannula (i.e., that portion which may be inserted into the patient) may be between 5 cm and 15 cm, or about 9 cm. In various preferred embodiments the cannula outer diameter may be between 15 and 30 french, between 20 and 26 french, or about 23 french.

As shown in FIGS. 3A-3E, the elongated body 16 has a slight bend 44, which may be between 10 to 60 degrees, just proximal of the distal end 20. The slight bend 44 may be positioned 1 cm to 8 cm proximal of the distal end. The bend 44 may be permanent, or may be controllable via controls known in the art. The bend 44 may be formed by a user via manual bending of the elongated body 16. For example, the elongated body 16 may have a location along its length (i.e., at the point where a bend is desired) where the elongated body 16 has increased flexibility (i.e., reduced resistance to bending), so that if a user applies a bending moment (either via direct application of force or via controls) to the elongated body 16, the bending moment will result in the bend 44 being formed at that position where the elongate body has increased flexibility.

The secondary opening 28 may be positioned just adjacent and proximal to the bend 44. The secondary opening 28 may comprise a valve 46 or friction/leakless fitting having an open position that permits fluid flow therethrough and a closed position wherein fluid flow therethrough is prevented. The valve 46 may be biased toward the closed position. The cannula 14 may include a substantially tubular extension 42 (which may be tapered for ease of insertion) having a distal end 50 and a proximal end 52. A tubular extension lumen 54 extends from a tubular extension distal opening 56 to a tubular extension proximal opening 58. The tubular extension distal end 50 is sized and positioned to be selectively advanced out of and back into the cannula primary lumen 22 via the secondary opening 28. A control line 60 may selectively control movement of the tubular extension 42 to effectuate advancement and retraction of the tubular extension distal end 50 through the secondary opening 28. FIGS. 3A-3E depict the tubular extension 42 in the stowed position.

When the tubular extension 42 is advanced out of the secondary opening 28, e.g., via the control line 60, it assumes a deployed configuration as depicted in FIGS. 4A-4E. In the deployed configuration, the tubular extension 42 forms a secondary fluid pathway from the cannula 14 via the tubular extension proximal opening 58 and extension lumen 54 that flows out of the tubular extension distal opening 56. The secondary fluid flow out of the tubular extension distal opening 56 may be in a different direction from the primary fluid flow from the cannula distal opening 26. In an embodiment where the secondary opening 28 comprises a valve 46, the tubular extension distal end 50 may be configured to move the valve 46 to the open position when the distal end 50 is advanced therethrough. The tubular extension 42 when deployed may prevent the blood vessel wall from collapsing against the secondary opening 28 and thereby preventing fluid flow therethrough.

Figure 5A:
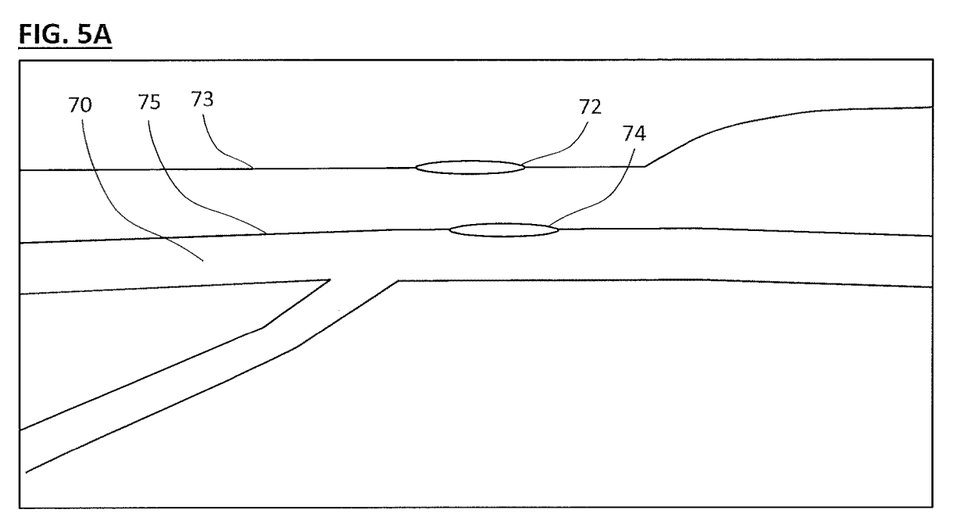
FIGS. 5A-5E depict side views of a procedure using the device, including advancement, positioning, deployment, retraction, and withdrawal of the device, respectively, according to an embodiment of the invention.
Figure 5B:
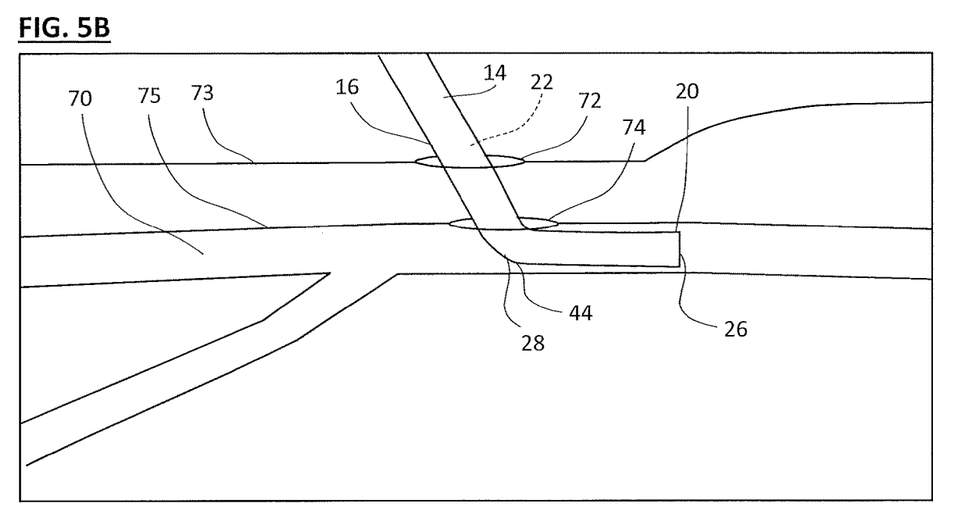

As depicted in FIG. 5A, a blood vessel 70, such as a femoral artery, is prepped by a surgeon or other user by forming a first incision 72 in the patient's skin 73 and a second incision 74 into the blood vessel wall 75. The incisions 72, 74 may be formed in a single maneuver, such as may be formed using a typical Seldinger technique. The cannula distal end 20 is advanced into the patient via the incisions 72, 74 until the distal opening 26, secondary opening 28, and bend 44 are all positioned within the blood vessel 70, as depicted in FIG. 5B. At this point, the surgeon or other user may provide primary perfusion via the distal opening 26, even without providing secondary perfusion flow via the secondary opening.

Note that primary perfusion flow may be provided to the distal opening 26 regardless of whether secondary flow is provided to the secondary opening 28 and/or whether the tubular extension 42 is in the deployed or retracted position. For example, a surgeon may initially provide only primary perfusion flow, and only provide secondary perfusion flow (e.g., by deploying the tubular extension 42) if the procedure exceeds a determined timeframe and/or responsive to patient monitoring. In an embodiment where the blood vessel is a femoral artery, the primary perfusion flow is toward the heart, and the secondary perfusion flow is toward the lower extremity/leg.

Figure 5C:
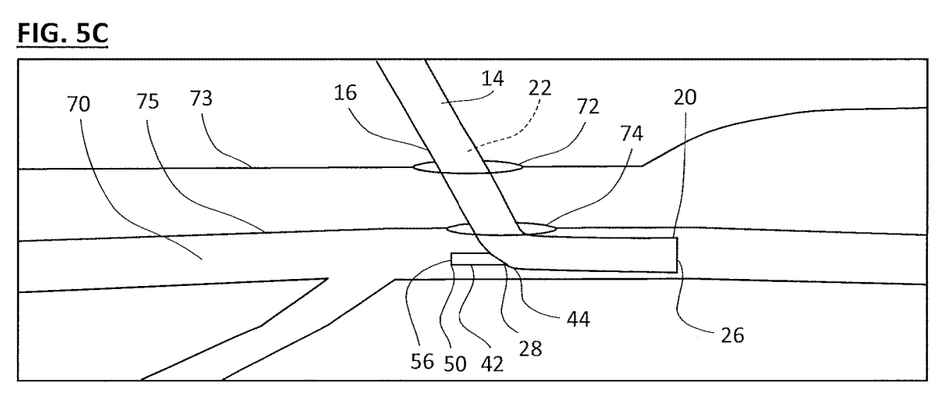

To deploy the tubular extension 42, the surgeon or other user can selectively advance the tubular extension 42 out of the secondary opening 28, e.g., via the control line 60, until the tubular extension distal opening 56 is advanced well out of the secondary opening 28. With the tubular extension 42 deployed, as depicted in FIG. 5C, a secondary fluid pathway is formed from the cannula 14 out to the tubular extension distal opening 56. The secondary perfusion flow can then be established via the tubular extension distal opening 56, with the secondary perfusion flow being opposite within the blood vessel to the direction of the primary perfusion flow.

Figure 5D:
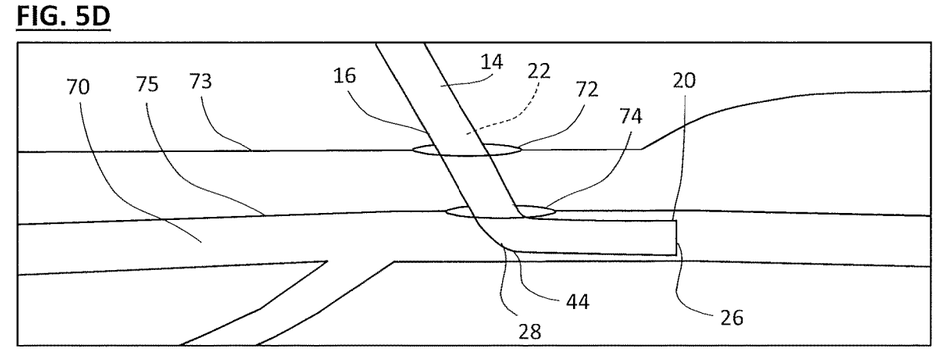
Figure 5E:
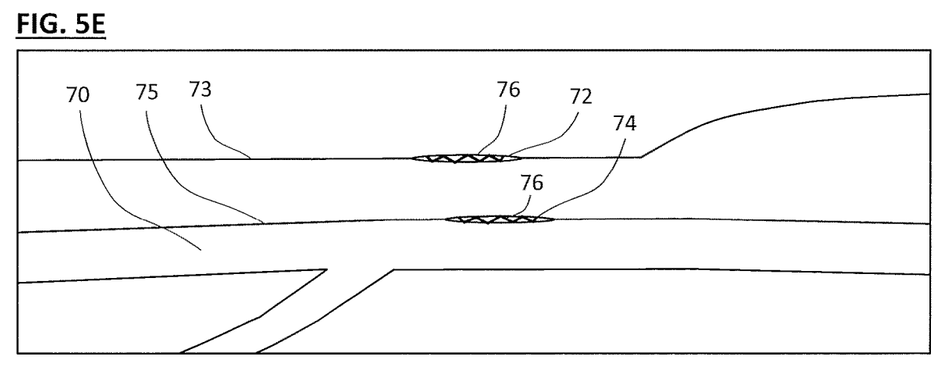

When secondary perfusion flow is no longer desired (e.g., when the cardiac procedure is completed), the surgeon or other user can retract the tubular extension 42 back into the cannula elongated body 16 via the secondary opening 28, as depicted in FIG. 5D. With the tubular extension 42 fully retracted, the cannula elongated body resumes a substantially smooth outer surface for easy withdrawal. The cannula 14 can then be withdrawn from the patient, as depicted on FIG. 5E. The incisions 72, 74 can be closed via various techniques, including known techniques such as via sutures 76, staples, adhesive, plugs, etc.

Figure 6A:
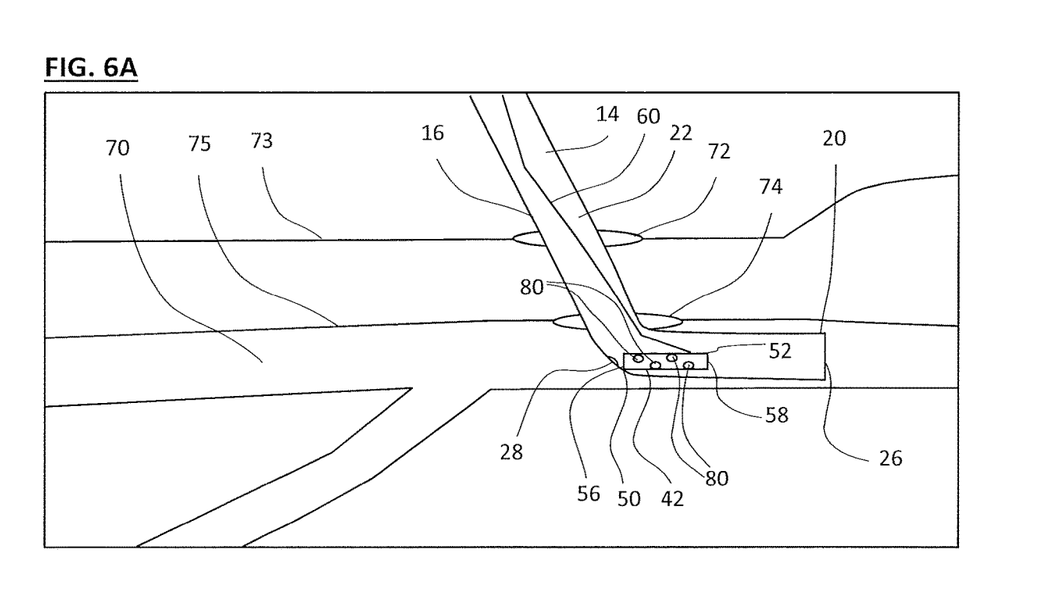
FIGS. 6A-6B depict side (cross-sectional) views of a device deployed in a patient's blood vessel in stowed and deployed positions, respectively, according to an embodiment of the invention.
Figure 6B:
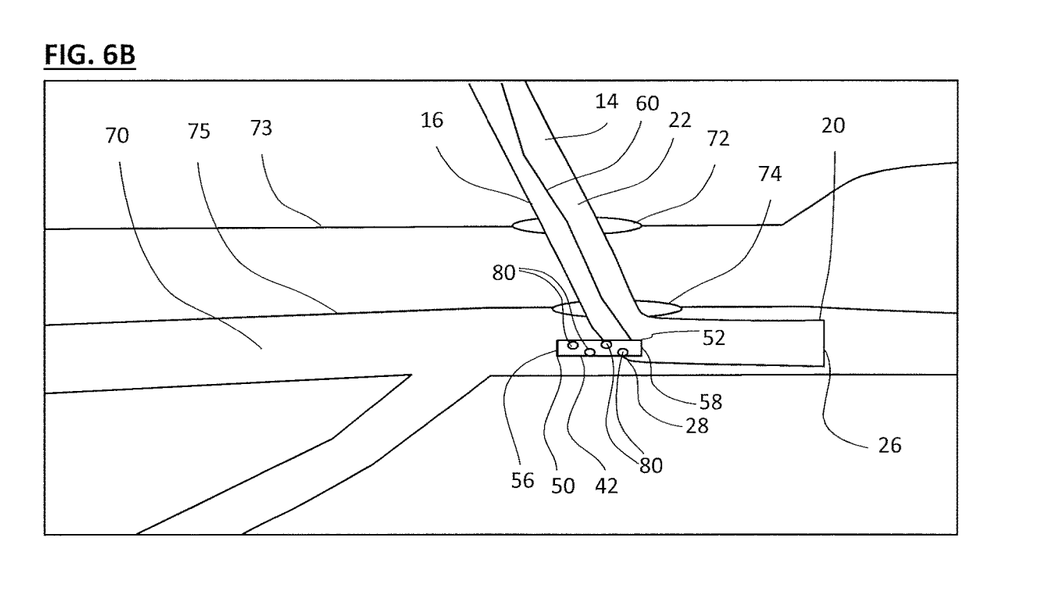

Another embodiment of the invention is depicted in FIGS. 6A-6B, wherein the tubular extension 42 may include one or more side openings 80 along the sides thereof, which may be in addition to or in lieu of the distal and/or proximal openings 56, 58. The side openings 80 may be spaced apart along the length and/or radius of the tubular extension. The side openings 80 may provide multiple fluid flow outputs so that if one or more of the side, distal, and/or proximal openings are blocked the remaining openings will still provide the desired fluid flow.

Figure 7A:
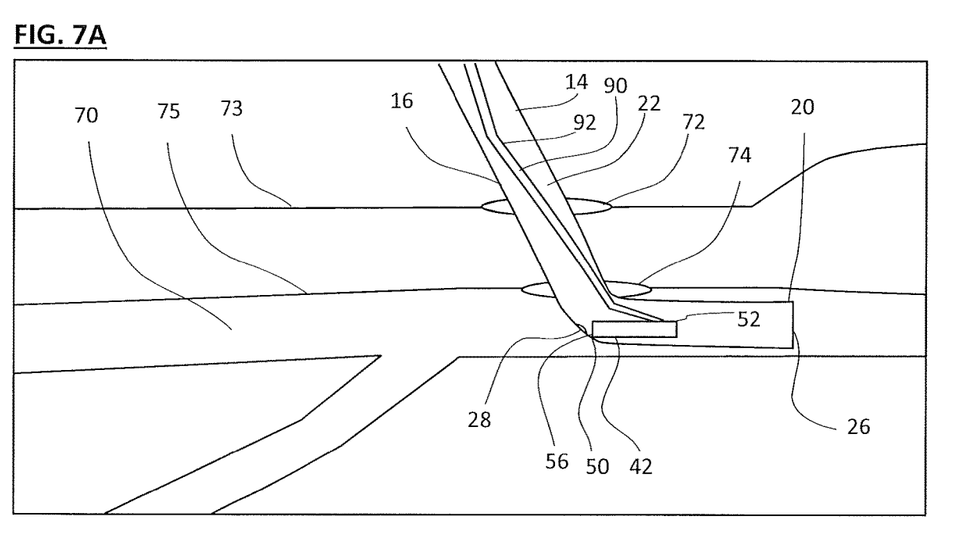
FIGS. 7A-7B depict side (cross-sectional) views of a device deployed in a patient's blood vessel in stowed and deployed positions, respectively, according to an embodiment of the invention.
Figure 7B:
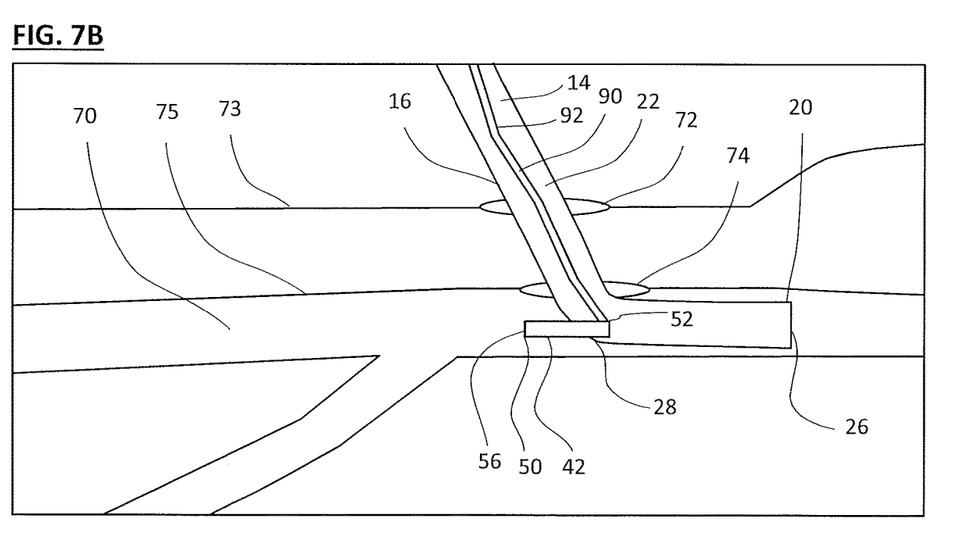

In the previously depicted embodiments of the invention, the secondary fluid flow via the tubular extension 42 is provided from the primary lumen 22 of the cannula 14. In another embodiment of the invention, depicted in FIGS. 7A and 7B, the secondary fluid flow is provided to the tubular extension 42 via a dedicated secondary lumen 90 in fluid connection with the tubular extension 42, e.g., via the proximal end 52 thereof. Note that the proximal end 52 may be closed to fluid flow from the primary lumen 22, so that no proximal opening (e.g., 58) is present that permits flow into or from the primary lumen 22. Flow to the secondary lumen 90 may be controlled by the user via controls, such as controls at the cannula proximal end 18 or at or adjacent another access port (e.g., a port such as the second proximal access port 17 of FIG. 1). The secondary lumen 90 may receive perfusion fluid from the primary perfusion fluid source 12 of the primary lumen 22, or from a separate secondary perfusion fluid source (e.g., via fluid provided through the second proximal access port 17 of FIG. 1). The secondary lumen 90 may be part of a tubular member 92 that also acts as a control line for the tubular extension in the manner that control line 60 performed in the embodiments of FIGS. 3A-3E, 4A-4E, and 6A-6B. The primary and secondary perfusion fluid sources may provide perfusion fluids having different drugs/drug levels, oxygenation, etc. For example, it may be desirable to provide cardiac-related drugs to the primary perfusion flow, but not to the secondary perfusion flow.

Note that the embodiments disclosed in the application may be combined into further embodiments without departing from the scope of the invention. For example, the secondary lumen 80 of FIGS. 7A-7B can be combined with the additional ports 80 of FIGS. 6A-6B, etc.

Note that the term "tubular" as used herein describes an elongated structure having an inner lumen therethrough, and is not meant to be limited to a specific cross-sectional form (e.g., circular, elliptical, rectangular, etc.) and/or to other specific structural limitations (such as constant radius/width along its length, varying radius/width along its length, etc.).

In closing it is understood that the embodiments of the invention disclosed herein are illustrative of the principles of the invention. Accordingly, the present invention is not limited to that precisely as shown and described in the present invention.

What is claimed is:

1. A method of providing perfusion to a limb of a patient during peripheral artery cannulization, the method comprising:

forming an incision in the patient from the patient's skin and into a selected blood vessel;

advancing a perfusion catheter into the selected blood vessel via the incision, the perfusion catheter comprising a proximal end; a distal end; an inner lumen extending from the proximal end to the distal end; a first opening at the distal end, the first opening configured to provide fluid flow from the inner lumen to a body lumen in a first direction; an elbow positioned along the perfusion catheter at a position proximal of the distal end; a second opening formed at the elbow and configured for providing fluid flow from the inner lumen to a body lumen in a second direction, wherein the second direction is different from the first direction; and a substantially tubular extension having a deployed configuration and a stowed configuration, wherein in the deployed configuration the substantially tubular extension extends at least partially out of the second opening, and in the stowed configuration the substantially tubular extension does not extend out of the second opening, and wherein in the deployed configuration the substantially tubular extension forms part of a direct fluid connection between the first opening and the inner lumen and the second opening;

positioning the perfusion catheter with the distal end and elbow within the selected blood vessel;

providing primary perfusion flow to the inner lumen and out of the first opening;

selectively providing secondary perfusion flow out of the second opening by selectively advancing the substantially tubular extension out of the second opening.

2. The method of claim 1, wherein the peripheral artery cannulization is performed during a bypass procedure, the method further comprising:

prior to selectively advancing the substantially tubular extension out of the second opening, monitoring the time of the bypass procedure.

3. The method of claim 2, wherein providing primary perfusion flow out of the first opening is initially performed prior to selectively providing secondary perfusion flow out of the second opening.

4. The method of claim 1, wherein the peripheral artery cannulization is performed during a bypass procedure.

5. The method of claim 1, wherein the first direction is opposite to the second direction.

6. The method of claim 1, wherein the primary perfusion flow is provided in a direction toward a heart of the patient, and the secondary perfusion flow is provided in a direction toward a distal portion of an extremity of the patient.

7. A method of providing perfusion to a selected blood vessel of a patient, comprising:

forming incisions in skin and a selected blood vessel of the patient;

advancing a perfusion cannula into the patient via the incisions, wherein the perfusion catheter comprises: a cannula elongated body; a proximal end; a distal end; an inner lumen extending through the cannula elongated body from the proximal end to the distal end; a first opening at the distal end, the first opening configured to provide primary fluid flow from the inner lumen to a body lumen in a first direction; an elbow positioned along the substantially tubular member at a position proximal of the distal end; a second opening formed at the elbow and configured for providing secondary fluid flow from the inner lumen to a body lumen in a second direction, wherein the second direction is different from the first direction; and a substantially tubular extension having a deployed configuration and a stowed configuration, wherein in the deployed configuration the substantially tubular extension extends at least partially out of the second opening, and in the stowed configuration the substantially tubular extension does not extend out of the second opening, and wherein in the deployed configuration the substantially tubular extension forms part of a direct fluid connection between the first opening and the inner lumen and the second opening;

positioning the distal opening, secondary opening, and bend within the blood vessel;

providing primary perfusion flow via the distal opening; and selectively advancing the substantially tubular extension out of the secondary opening to thereby provide secondary perfusion flow via the secondary opening.

8. The method of claim 7, wherein providing secondary perfusion flow occurs responsive to patient monitoring.

9. The method of claim 7, wherein the primary perfusion flow is opposite to the secondary perfusion flow.

10. The method of claim 9, wherein the primary perfusion flow is toward a heart of the patient, and the secondary perfusion flow is toward a distal portion of an extremity of the patient.

11. The method of claim 10, wherein the blood vessel is a femoral artery, the primary perfusion flow is toward the heart of the patient, and the extremity is a lower leg of the patient.

12. The method of claim 7, further comprising:
retracting the substantially tubular extension back into the cannula elongated body via the secondary opening; and
withdrawing the perfusion cannula from the patient.

13. The method of claim 12, further comprising:
closing the incisions via sutures, staples, adhesives, or plugs.

14. A method of providing perfusion to a limb of a patient, comprising:
forming an incision in the patient from the patient's skin and into a selected blood vessel;
advancing a perfusion catheter into the selected blood vessel via the incision, the perfusion catheter comprising an elongated body; a proximal end; a distal end; an inner lumen extending inside the elongated body from the proximal end to the distal end; a first opening at the distal end, the first opening configured to provide primary fluid flow from the inner lumen to a body lumen in a first direction; an elbow positioned along the elongated body at a position proximal of the distal end; a second opening formed at the elbow and configured for providing secondary fluid flow from the inner lumen to a body lumen in a second direction, wherein the second direction is different from the first direction; and a substantially tubular extension having a tubular extension distal opening, tubular extension proximal opening, a deployed configuration, and a stowed configuration, wherein the perfusion catheter is advanced with the distal end advanced in an insertion direction, wherein in the deployed configuration the tubular extension distal opening extends at least partially out of the second opening, and in the stowed configuration the tubular extension distal opening does not extend out of the second opening;

positioning the perfusion catheter with the distal end and elbow within the selected blood vessel;

providing primary perfusion flow to the inner lumen and out of the first opening; and selectively advancing the substantially tubular extension and tubular extension distal opening out of the second opening to thereby selectively provide secondary perfusion flow to the inner lumen and out of the second opening.

15. The method of claim 14, wherein the perfusion is provided during a bypass procedure, and further comprising:
prior to selectively advancing the substantially tubular extension and tubular extension distal opening out of the second opening, monitoring the time of the bypass procedure or patient parameters of oxygenation, blood pressure, or pulse.

16. The method of claim 14, wherein the insertion direction is the same as the first direction.

17. The method of claim 16, wherein the second direction is opposite to the insertion direction.

18. The method of claim 14, wherein the primary perfusion flow is toward a heart of the patient, and the secondary perfusion flow is toward a distal portion of the limb of the patient.

19. The method of claim 18, wherein the blood vessel is a femoral artery, and the limb is a leg of the patient.

20. The method of claim 14, wherein the substantially tubular extension is biased toward the stowed configuration.

* * * * *